United States Patent [19]

Berger et al.

[11] Patent Number: 4,465,823
[45] Date of Patent: Aug. 14, 1984

[54] ETHYLENICALLY UNSATURATED CROSSLINKABLE TRANSPARENT POLYAMIDE

[75] Inventors: Joseph Berger, Basel; Josef Pfeifer, Therwil, both of Switzerland; Dieter Reinehr, Kandern, Fed. Rep. of Germany

[73] Assignee: Ciba-Geigy Corporation, Ardsley, N.Y.

[21] Appl. No.: 461,050

[22] Filed: Jan. 26, 1983

[30] Foreign Application Priority Data

Jan. 29, 1982 [CH] Switzerland .......................... 561/82

[51] Int. Cl.³ .............................................. C08G 69/26
[52] U.S. Cl. ................................ 528/345; 204/159.11; 204/159.18; 204/159.19; 525/421; 528/336; 528/339; 528/339.3; 528/339.5; 528/347; 260/404.5
[58] Field of Search ............... 528/345, 347, 339, 336, 528/339.3, 339.5, ; 260/404.5 PA, 404.5 R

[56] References Cited

U.S. PATENT DOCUMENTS

| | | | |
|---|---|---|---|
| 4,195,165 | 3/1980 | Pfeifer et al. | 528/346 |
| 4,210,742 | 7/1980 | Pfeifer et al. | 528/346 |
| 4,210,743 | 7/1980 | Pfeifer et al. | 528/347 |
| 4,297,480 | 10/1981 | Pfeifer et al. | 528/346 |
| 4,377,683 | 3/1983 | Pfeifer et al. | 528/336 |

OTHER PUBLICATIONS (Chem. Abstracts 91977k, vol. 81, (1974).

*Primary Examiner*—Harold D. Anderson
*Attorney, Agent, or Firm*—Harry Falber

[57] ABSTRACT

Novel crosslinkable transparent polyamides are described which are obtained by the condensation of diamines of the formula

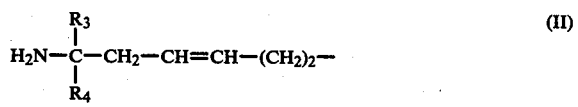

(II)

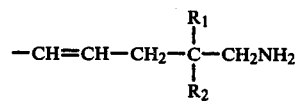

with aromatic and/or aliphatic dicarboxylic acids or amide-forming derivatives thereof, preferably in the presence of an inorganic or organic phosphorus compound as an accelerator. In the formula, $R_1$ to $R_4$ are defined as in patent claim 1. The novel polyamides are suitable for the production of solvent-resistant coatings on various substrates, for the production of images under the action of light, in particular when mixed with polythiols and photoinitiators or photosensitizers, or for the production of transparent mouldings.

7 Claims, No Drawings

ETHYLENICALLY UNSATURATED CROSSLINKABLE TRANSPARENT POLYAMIDE

The invention relates to novel crosslinkable transparent polyamides, processes for their preparation and their use, particularly in crosslinkable mixtures of substances containing polythiols.

Polyamides which can be crosslinked via C=C double bonds are known, for example, from Japanese Patent Publication No. 9677/67, German Offenlegungsschrift No. 3,037,488 and Vysokomol. Soedin, series B, 16, 97 (1974). These known polyamides are prepared using, as diamine components, unsubstituted 1,11-diaminoundecenes, monounsaturated or diunsaturated, unsubstituted α,ω-diamines having 12 C atoms, such as 1,12-diaminododecane-5,9-cis,transdiene, or 1,8-diamino-octa-2,6-dienes which can be unsubstituted or substituted by two or four methyl groups. These previously known polyamides are crystalline products. Non-crosslinkable transparent polyamides from saturated substituted diamines, for example 1,10-diamino-decanes or 1,11-diamino-undecanes substituted in the 1,10-positions, and from aromatic or aliphatic dicarboxylic acids are described, for example, in German Offenlegungsschriften Nos. 2,846,459, 2,846,501 and 2,846,514, and also in European Patent Publication No. 12,712.

The invention relates to novel transparent polyamides which consist of repeat structural units of the formula I

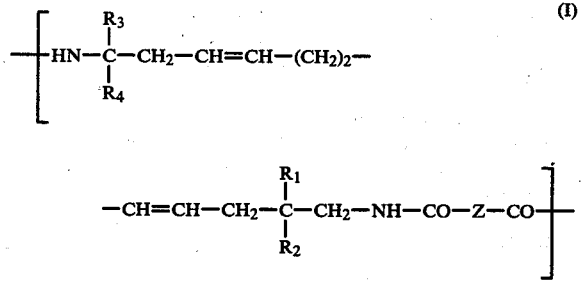

in which $R_1$ is $C_{1-12}$-alkyl, $R_2$ is hydrogen or $C_{1-12}$-alkyl, $R_3$ is $C_{1-12}$-alkyl, cycloalkyl having 4–12 ring C atoms, aralkyl having 7 or 8 C atoms, substituted or unsubstituted aryl or, if $R_4$ is hydrogen, —CH=CH-alkyl or —C(alkyl)=CH—alkyl, each having 1–4 C atoms in the alkyl groups, $R_4$ is hydrogen, $C_{1-12}$-alkyl, cycloalkyl having 4–12 ring C atoms, aralkyl having 7 or 8 C atoms or substituted or unsubstituted aryl, or $R_1$ and $R_2$ and/or $R_3$ and $R_4$ together are alkylene having 3–11 C atoms, and the symbols Z in the various structural units of the formula I are identical or different radicals of a saturated or unsaturated aliphatic or aromatic dicarboxylic acid.

Alkyl groups $R_1$ to $R_4$ can be straight-chain or branched. Alkyl groups $R_1$, $R_2$ and $R_4$ preferably have 1–5 C atoms and are straight-chain. Alkyl groups $R_3$ advantageously have 1–7 C atoms and especially 1–5 C atoms. Examples of alkyl groups $R_1$ to $R_4$ are: the methyl, ethyl, n-propyl, isopropyl, n-, sec.- and tert.-butyl, n-pentyl, 2-pentyl or 3-pentyl, n-hexyl, 2-heptyl or 3-heptyl, n-octyl, n-decyl and n-dodecyl groups.

If $R_3$ is a group —CH=CH—alkyl or —C(alkyl)=CH—alkyl, the alkyl groups in these substituents are preferably straight-chain and are especially methyl or ethyl.

Cycloalkyl groups $R_3$ and $R_4$ can be unsubstituted or substituted by $C_{1-4}$-alkyl groups. They are especially cycloalkyl substituted by a methyl or ethyl group. Preferably, however, cycloalkyl groups $R_3$ and $R_4$ are unsubstituted and have 5–8 ring C atoms. The cyclopentyl group and, in particular, the cyclohexyl group are particularly preferred.

Possible aralkyl groups $R_3$ and $R_4$ are, in particular, the benzyl, methylbenzyl or phenylethyl group. If $R_3$ or $R_4$ is substituted aryl, possible substituents are, in particular, alkyl groups having 1–4 and especially 1 or 2 C atoms. Aryl groups $R_3$ and $R_4$ can carry several alkyl groups, but are preferably substituted by only one alkyl group. Particular preference is given to the 1-naphthyl or 2-naphthyl group, phenyl substituted by an alkyl group having 1–4 and particularly 1 or 2 C atoms, and, very particularly, unsubstituted phenyl.

Alkylene groups represented by $R_1$ and $R_2$ and/or $R_3$ and $R_4$ together preferably have 4–7 C atoms. These are especially the tetramethylene group and, very particularly, the pentamethylene group.

The polyamides according to the invention can be prepared, in a manner known per se, by reacting a diamine of the formula II

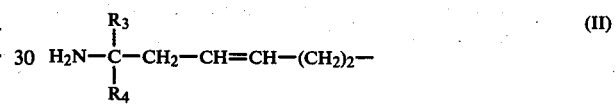

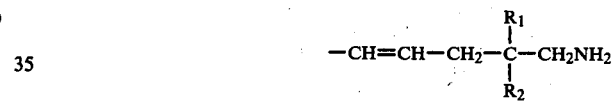

with a dicarboxylic acid of the formula III

an amide-forming derivative thereof or a mixture of various dicarboxylic acids of the formula III or of amide-forming derivatives thereof. In these formulae, $R_1$ to $R_4$ and Z are as defined above.

Amide-forming derivatives of the dicarboxylic acids of the formula III which can be used are, for example, the corresponding dihalides, in particular the dichlorides, dinitriles, dialkyl esters or diaryl esters, particularly diphenyl esters and dialkyl esters having 1–4 C atoms in each of the alkyl moieties.

In general, it is advantageous to carry out the polycondensation in the presence of a phosphorus compound as an accelerator. Shorter reaction times are thereby achieved and the polycondensation can be carried out at high temperatures, for example in the melt. The invention therefore also relates to transparent polyamides which can be obtained by subjecting a diamine of the formula II to polycondensation, as described above, with a dicarboxylic acid of the formula III, an amide-forming derivative thereof or a mixture of various dicarboxylic acids of the formula III or of amide-forming derivatives thereof, in the presence of a phosphorus compound containing 30 to 1,000 ppm, preferably 80 to 500 ppm, of phosphorus, based on the sum of the condensation components.

Phosphorus compounds which can be used are either inorganic or organic compounds, such as oxyacids of phosphorus and derivatives thereof, for example esters of amides, or phosphinic and phosphonic acids and derivatives thereof.

Examples of possible inorganic phosphorus compounds are phosphoric acid, phosphorous acid and hypophosphorous acid and derivatives thereof, such as mono-ammonium phosphate, di-ammonium hydrogenphosphate, $NH_4H_2PO_3$ and $NH_4H_2PO_2$, esters and amides, in particular alkyl esters having 1-8 C atoms in each of the alkyl groups, and phenyl esters, or dialkylamides having 1-4 C atoms in each of the alkyl groups. Examples of such derivatives are: diethyl phosphite, dibutyl phosphite, triphenyl phosphite, trimethyl phosphate, triethyl phosphate, tributyl phosphate, tri-isobutyl phosphate, triphenyl phosphate, tricresyl phosphate and hexamethylphosphoric acid triamide. Pyrophosphoric acid and polyphosphoric acids are also suitable.

Examples of suitable organic phosphorus compounds are monophosphonic and polyphosphonic acids, phosphinic acids and derivatives thereof. Examples of polyphosphonic acids are

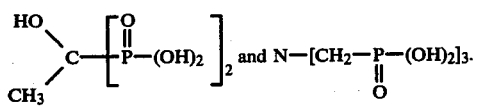

Especially suitable monophosphonic acids and monophosphinic acids are those of the formulae IVa and IVb

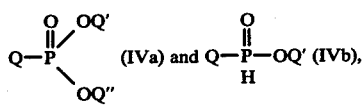

in which Q is substituted or unsubstituted aryl, aralkyl or alkyl and Q' and Q" independently of one another are hydrogen or can be defined in the same way as Q, but are preferably hydrogen or $C_{1-4}$-alkyl. Preferred compounds are those of the formulae IVa and IVb in which Q is phenyl or

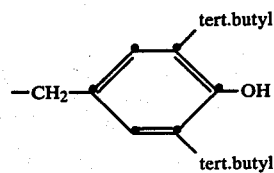

Particularly preferably, diethyl 2,6-di-tert.-butyl-p-cresylphosphonate is used as the organic phosphorus compound or phosphoric acid or $NH_4H_2PO_2$ is used as the inorganic phosphorus compound.

Preferably, the polyamides according to the invention are prepared by the melt polycondensation process in several steps. In this process, the reaction components, preferably salts of a dicarboxylic acid of the formula III and of a diamine of the formula II, are pre-condensed in essentially stoichiometric amounts, under pressure, at temperatures of between about 220° and 300° C., in the melt, under an inert gas such as nitrogen. The pre-condensate can then be condensed further, at temperatures of between 220° and 300° C., at normal pressure and advantageously also in an inert gas atmosphere, until the polyamides according to the invention have formed. Under certain circumstances, it can be advantageous to apply a vacuum after the polycondensation has ended, in order to degas the polyamide. This process is particularly suitable for the preparation of polyamides using aliphatic dicarboxylic acids having 6–36 C atoms and/or aromatic dicarboxylic acids.

The polyamides according to the invention can also be prepared by the polycondensation of diamines of the formula II with essentially stoichiometric amounts of an activated ester of a dicarboxylic acid of the formula III, in the melt. Suitable activated esters are, in particular, the corresponding diphenyl esters. In this process, the reaction temperatures are generally between about 230° and 300° C. This process is particularly preferred if $R_4$ is $C_{1-12}$-alkyl or $R_3$ and $R_4$ together are $C_{3-11}$-alkylene.

Finally, the polyamides according to the invention can be prepared, also in a manner known per se, by solvent polycondensation, preferably using acid halides and in the presence of acid-binding agents, or by interfacial polycondensation. These processes are preferred if aliphatic dicarboxylic acids having 4 or 5 C atoms are used.

In general, in the polycondensation reactions, it is advantageous also to use polymerisation inhibitors, for example hydroquinone or sterically hindered phenols such as di-tert.-butyl-p-cresol, in order to prevent premature crosslinking.

Preferred polyamides are those in which $R_1$ is $C_{1-5}$-alkyl, $R_2$ is hydrogen or $C_{1-5}$-alkyl, or $R_1$ and $R_2$ together are alkylene having 4–7 C atoms, $R_3$ is $C_{1-7}$-alkyl, $C_{5-8}$-cycloalkyl, unsubstituted phenyl or, if $R_4=H$, $-C(C_2H_5)=CH-CH_3$, $R_4$ is hydrogen or $C_{1-5}$-alkyl and Z is the radical of terephthalic acid, of isophthalic acid, of a saturated aliphatic dicarboxylic acid having 6–12 C atoms and/or of an unsaturated aliphatic dicarboxylic acid having 6–36 C atoms. Particularly preferred polyamides are those in which $R_1$ is $C_{1-5}$-alkyl, $R_2$ is hydrogen or $C_{1-5}$-alkyl, or $R_1$ and $R_2$ together are alkylene having 4–7 C atoms, $R_3$ is $C_{1-5}$-alkyl, unsubstituted phenyl or, if $R_4=H$, $-C(C_2H_5)=CHCH_3$, $R_4$ is hydrogen or methyl and Z is the radical of terephthalic acid, of isophthalic acid, of a saturated aliphatic dicarboxylic acid having 6–12 C atoms and/or of an unsaturated aliphatic dicarboxylic acid having 36 C atoms (dimeric acid), and in particular those in which $R_1$ is methyl or ethyl, $R_2$ is hydrogen, methyl or ethyl, $R_3$ is $C_{1-5}$-alkyl or unsubstituted phenyl, $R_4$ is hydrogen or methyl and Z is the radical of terephthalic acid, of isophthalic acid and/or of a saturated aliphatic dicarboxylic acid having 6–10 C atoms.

Amongst the homopolyamides, those in which $R_1$ and $R_2$ are methyl, $R_3$ is isopropyl, $R_4$ is hydrogen and Z is the radical of terephthalic acid, of isophthalic acid or of adipic acid are very particularly preferred.

However, very particular preference is given to copolyamides in which $R_1$ and $R_2$ are methyl, $R_3$ is isopropyl, $R_4$ is hydrogen and Z is the radical of terephthalic acid in 50 to 90%, particularly 60 to 85%, of the structural units of the formula I and the radical of adipic acid in 50 to 10%, particularly 45 to 15%, of the structural units of the formula I, or to polyamides which can be obtained in the presence of a phosphorus compound containing 80 to 500 ppm of phosphorus, in particular $H_3PO_4$, $NH_4H_2PO_2$ or diethyl 2,6-di-tert.-butyl-p-cresylphosphonate, and in which $R_1$ and $R_2$ are methyl, $R_3$ is isopropyl, $R_4$ is hydrogen and Z is the radical of terephthalic acid in 50 to 90% by weight, particularly 60 to 85% by weight, of the compound of the formula III and the radical of adipic acid in 50 to 10% by weight, particularly 40 to 15% by weight, of the compound of the formula III, the percentages by weight being based on identical functional groups of the dicarboxylic acids.

The dicarboxylic acids of the formula III and their amide-forming derivatives are known. The diamines of the formula II can be prepared either by reducing compounds of the formula IIa

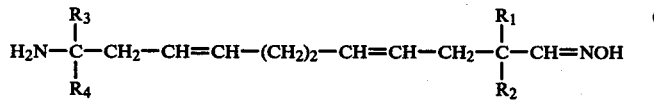

directly to give compounds of the formula II, or first dehydrating the compounds of the formula IIa to give compounds of the formula IIb

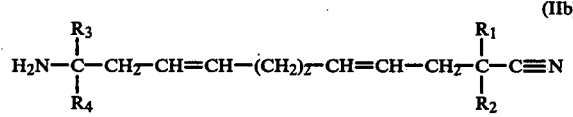

and then reducing the compounds of the formula IIb to give compounds of the formula II, $R_1$ and $R_4$ being as defined under the formula I.

The reduction of the compounds of the formula IIa or IIb to give compounds of the formula I can be carried out in a manner known per se, for example by means of Bouveault-Blanc reduction with sodium metal and alcohols, if appropriate in the presence of an inert organic solvent, for example aromatic hydrocarbons such as benzene, toluene or xylene.

If appropriate, the dehydration of the compounds of the formula IIa to give compounds of the formula IIb can be carried out chemically or thermally, also in a manner known per se. The starting materials of the formula IIa are known and can be prepared by the process described in European Patent Specification No. 11,599.

The polyamides according to the invention are suitable, for example, for the production of solvent-resistant coatings on various materials, in particular metals such as aluminium, copper and steel, for the production of images under the action of light on various inorganic or organic substrates, or for the production of transparent mouldings, for example by the injection-moulding or extrusion process. Examples of suitable substrates for the production of images are glass, metals and metal oxides, such as aluminium, aluminium oxide and copper, ceramics, paper and high-molecular organic materials. Possible high-molecular organic materials are natural and synthetic polymers, for example cellulose materials such as cellulose acetates, cellulose propionates, cellulose butyrates and cellulose ethers, cross-linked epoxy resins, polyacetals, polyphenylene oxides, saturated polyamides, polyolefins such as polyethylene and polypropylene and copolymers thereof, vinyl polymers such as polyvinyl chloride, polyvinyl acetate, polyvinylalcohol and copolymers thereof, and, in particular, polyesters.

The polyamides according to the invention can be readily crosslinked under the action of heat or photochemically, if appropriate with the addition of free-radical initiators known per se. Thermal crosslinking is generally carried out at temperatures of between 80° and 180° C., particularly of between 120° and 160° C. The free-radical initiators are advantageously used in amounts of 0.01 to 5% by weight, preferably 0.01 to 1.5% by weight, based on the total weight of the polyamide.

Examples of suitable initiators are inorganic or organic peroxides or azo compounds, for example hydrogen peroxide, potassium peroxydisulfate, tert.-butyl hydroperoxide, di-tert.-butyl peroxide, peracetic acid, dibenzoyl peroxide, diacyl peroxides, cumene hydroperoxide, tert.-butyl perbenzoate, tert.-alkyl peroxydicarbonates and $\alpha,\alpha'$-azoisobutyronitrile.

Photochemical crosslinking is preferably carried out in the presence of polythiols and photoinitiators.

The invention therefore also relates to crosslinkable mixtures of substances containing
  (a) a polyamide according to the invention,
  (B) 5 to 80% by weight, particularly 30 to 65% by weight, based on the polyamide, of a polythiol having at least two thiol groups per molecule, and
  (C) 0.1 to 10% by weight, particularly 1 to 5% by weight, based on the polyamide, of an initiator which can be cleaved under the action of light to give free radicals, or of a photosensitiser. $R_1$ to $R_4$ are preferably defined as under the formula I.

Examples of suitable photosensitisers (C) are benzophenone, acetophenone, 1,4-diacetylbenzene, xanthone, thioxanthones, 2-acetonaphthene, 1-acetonaphthol, Michler's ketone, thiophene, benzanthrone and benzoin ethers. Free-radical intiators of the type mentioned above can be used as intiators. Preferably, benzophenone or thioxanthone is used as the photosensitiser.

Suitable polythiols are described, for example, in U.S. Pat. No. 3,824,104. Preferred compounds are those of the formulae V and VI $$Q_1\text{—}(SH)_n \qquad (V)$$

and $$Q_1\text{—}(OCO\text{—}Q_2\text{—}SH)_{n1} \qquad (VI).$$

In these formulae, n and $n_1$ are an integer equal to at least 2, $Q_1$ is an n-valent or $n_1$-valent organic radical having no C—C multiple bonds, which can also contain heteroatoms, and $Q_2$ is a divalent radical having no C—C multiple bonds.

n is preferably 2 and $Q_1$ in the formula V is especially phenylene, tolylene, xylylene or —$C_mH_{2m}$—, with m=2–12. Examples of compounds of the formula V are: phenylene-1,4-dithiol, tolylene-2,4-dithiol, m-xylylene-2,5-dithiol, ethanedithiol, tetramethylenedithiol, hexamethylenedithiol and decamethylenedithiol.

$n_1$ is preferably 2, 3 or 4. $Q_2$ is especially —$C_pH_{2p}$—, with p=1–3, particularly —$CH_2$—, —$CH_2CH_2$— or —$CH(CH_3)$—. $Q_1$ in the formula VI is preferably a radical —$C_mH_{2m}$—, in particular —$CH_2CH_2$—, —$CH_2CHCH_2$— or $C(CH_2$—$)_4$. Examples of compounds of the formula VI are ethylene glycol bis-(thioglycolate), ethylene glycol bis(3-mercaptopropionate), trimethylolpropane tris-(thioglycolate), trimethylol tris-(3-mercaptopropionate), pentaerythritol tetrakis-(thioglycolate) and pentaerythritol tetrakis-(3-mercaptopropionate). The compounds of the formulae V and VI can also be polymers such as polypropylene glycol bis-(3-mercaptopropionate). Other suitable compounds are low-molecular thioplasts with mercaptan end groups, which are generally present as mixtures with various organic radicals, for example polymers of bis-(ethyleneoxy)-methane with disulfide bridges from the Thiokol Chemical Corp. (cf., for example, U.S. Pat. Nos. 2,402,977 and 2,875,182). Preferred compounds of the formula VI are those in which $Q_1$, $Q_2$ and $n_1$ have the preferred definitions given above, and very particularly pentaerythritol tetrakis-(3-mercaptopropionate).

Such crosslinkable compositions of substances can also contain other additives known per se, such as stabilisers, antioxidants, dyes, pigments, antistatic agents or flame retarders, plasticisers and fillers.

The said mixtures of substances containing polythiols are suitable, in particular, for the production of printed circuits.

Photochemical crosslinking can be carried out using any suitable light sources, for example xenon lamps, metal halide lamps and particularly high-pressure and medium-pressure mercury lamps.

The transparent polyamides according to the invention are distinguished by low water uptake, high resistance to hydrolysis and/or good dimensional stability under the action of moisture. Furthermore, they give very strongly adhering, solvent-resistant coatings, especially on metals, and-in contrast to previously known, unsaturated polyamides-have a good compatibility with polythiols. By virtue of their good solubility in various organic solvents, such as chloroform, ethanol and N,N-dimethylformamide, films and coatings can readily be produced on metal or plastic surfaces.

EXAMPLE 1

62.8 g of 2,2-dimethyl-11-isopropyl-1,11-diamino-undeca-4,8-diene, 36.4 g of adipic acid, 0.25 ml of a 10% aqueous $NH_4H_2PO_2$ solution and 0.5 g of di-tert.-butyl-p-cresol are pre-condensed in an autoclave for 90 minutes, in a nitrogen atmosphere, then condensed further for 4 hours in an open polycondensation vessel, in a stream of nitrogen, and finally post-condensed for 1 hour in a high vacuum. All polycondensation steps are carried out at 250° C.

Elementary analysis of the polyamide obtained: Calculated: C 72.88%; H 10.57%; N 7.73%. Found: C 70.22%; H 10.47%; N 7.45.
Content of end groups: —COOH: 0.16 milliequivalent/g; —$NH_2$: 0.04 milliequivalent/g. Glass transition temperature (Tg, determined in a differential scanning calorimeter)=45° C.; reduced viscosity $\eta$red. =0.70 dl/g (measured on a 0.5% solution in m-cresol at 25° C.).

The diamine used can be prepared as follows:
80 g (0.3 mol) of 2,2-dimethyl-11-isopropyl-11-amino-undeca-4,8-dienaldoxime are treated with 100 ml of glacial acetic acid, with stirring. HCl gas is then passed in up to saturation and 30.6 g (0.3 mol) of acetic anhydride are added dropwise in the course of 15 minutes. The reaction mixture is heated for 4 hours under reflux, the glacial acetic acid is distilled off and the residue is dissolved in water. After the solution has been rendered basic with sodium hydroxide solution, the organic phase which separates out is taken up in toluene and the mixture is distilled. This gives 68.5 g (0.276 mol) of 1,1-dimethyl-10-isopropyl-10-amino-deca-3,7-diene-nitrile, corresponding to a yield of 92% of theory; boiling point: 94° C./3 Pa.

23 g (1 mol) of sodium are added to 150 ml of toluene and the mixture is heated until the sodium melts. The source of heat is then removed and the mixture is stirred until the sodium is finely divided as a grey dispersion. A solution of 53 g (0.214 mol) of 1,1-dimethyl-10-isopropyl-10-amino-deca-3,7-diene-nitrile in 100 ml of isopropanol is then added dropwise to this mixture. The resulting mixture is boiled under reflux for a further 3 hours and treated with 200 ml of water, and the organic phase is separated off. After the solvent has been distilled off, 44 g (0.175 mol) of 2,2-dimethyl-11-isopropyl-1,11-diamino-undeca-4,8-diene are obtained, corresponding to a yield of 81.5% of theory; boiling point: 86° C./1 Pa; $n_d^{20}$=1.4810.

EXAMPLES 2a and 2b

In the manner described in Example 1, 38.21 g of terephthalic acid are subjected to polycondensation with 58.06 g of 2,2-dimethyl-11-isopropyl-1,11-diaminoundeca-4,8-diene, or 29.26 g of isophthalic acid are subjected to polycondensation with 46.0 g of 2,2-dimethyl-11-isopropyl-1,11-diamino-undeca-4,8-diene in the presence of 0.25 ml of a 10% aqueous $NH_4H_2PO_2$ solution and 0.5 g of di-tert.-butyl-p-cresol. The properties of the polyamide obtained are given in the table which follows.

EXAMPLE 3

Preparation of a salt of terephthalic acid (TPA) and 2,2-dimethyl-11-isopropyl-1,11-diamino-undeca-4,8-diene (undecadiene-diamine=UDD):

97.1 g of terephthalic acid are suspended in 2,400 ml of water and 600 ml of methanol. 148.9 g of UDD are added dropwise to the resulting suspension, at the reflux temperature, a homogeneous solution being formed. After boiling for 60 minutes, the solution is left to cool to 0°-5° C. After 24 hours, the salt formed is filtered off and dried at 80° C. in vacuo. Yield: 180 g (73.6% of theory).

60 g of the salt thus obtained are subjected to polycondensation as described in Example 1. The properties of the polyamide obtained are given in the table which follows.

EXAMPLE 4

30 g of the salt of TPA and UDD obtained according to Example 3 are subjected to polycondensation as described in Example 1, but the last condensation step in vacuo is omitted. The properties of the polyamide obtained are given in the table which follows.

EXAMPLE 5

Preparation of a salt of adipic acid (AA) and UDD:
36.2 g of adipic acid are dissolved in 270 ml of absolute ethanol at 50° C. After the solution has cooled, 69.7 g of UDD in 107 ml of absolute ethanol are added. The salt, which precipitates after two thirds of the solvent has been stripped off and the remainder has been cooled to 0°-5° C., is filtered off and dried in vacuo at 20° C.
Yield: 82.5 g (85.3% of theory).

56.0 g of the salt of TPA and UDD obtained according to Example 3 and 14.0 g of the above salt of adipic acid and UDD are subjected to polycondensation as described in Example 1, but the last condensation step in vacuo is omitted. The properties of the polyamide obtained are given in the table which follows.

EXAMPLE 6

30.0 g of the salt of TPA and UDD prepared according to Example 3, and 30.0 g of the salt of adipic acid and UDD prepared according to Example 5, are subjected to polycondensation as described in Example 1, but the polycondensation step in vacuo is omitted. The properties of the polyamide obtained are given in the table which follows.

EXAMPLE 7

Example 6 is repeated, but 54.0 g of the salt of TPA and UDD and 6.0 g of the salt of adipic acid and UDD are used. The properties of the polyamide obtained are given in the table which follows.

The polycondensation reactions according to the Examples 3–7 are all carried out in the presence of 0.25 ml of a 10% aqueous $NH_4H_2PO_2$ solution and 0.5 g of di-tert.-butyl-p-cresol.

EXAMPLE 8

50.0 g of UDD, 28.98 g of adipic acid, 79 mg of the compound of the formula

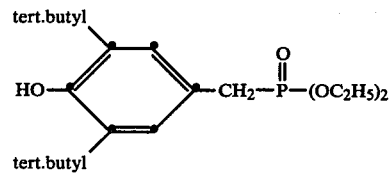

and 0.4 g of di-tert.-butyl-p-cresol are subjected to polycondensation as described in Example 1.

Elementary analysis of the polyamide obtained: Calculated: C 72.88%; H 10.57%; N 7.79%. Found: C 71.2%; H 10.51%; N 7.68%.

Content of end groups: —COOH: 0.15 milliequivalent/g; —NH₂: 0.05 milliequivalent/g. The other properties of the polyamide obtained are given in Table I which follows.

TABLE I

| Polyamide according to Example No. | Condensation components | Glass transition temperature Tg (°C.)** | Reduced viscosity η red dl/g* |
|---|---|---|---|
| 2a | 38.21 g of TPA, 58.06 g of UDD | 108 | 0.23 |
| 2b | 29.26 g of IPA, 46.0 g of UDD | 100 | 0.34 |
| 3 | 60.0 g of TPA/UDD salt | 114 | insoluble |
| 4 | 30.0 g of TPA/UDD salt | 115 | 0.78 |
| 5 | 56.0 g of TPA/UDD salt 14.0 g of AA/UDD salt | 105 | 0.72 |
| 6 | 30.0 g of TPA/UDD salt 30.0 g of AA/UDD salt | 73 | 0.75 |
| 7 | 54.0 g of TPA/UDD salt 6.0 g of AA/UDD salt | 101 | 0.78 |
| 8 | 28.98 g of AA 50.0 g of UDD | 42 | 0.68 |

TPA = terephthalic acid
AA = adipic acid
UDD = 2,2-dimethyl-11-isopropyl-1,11-diamino-undeca-4,8-diene
IPA = isophthalic acid
*measured on a 0.5% solution in m-cresol at 25° C.
**determined in a differential scanning calorimeter (DSC)

EXAMPLE 9

7.03 g of 92% pure 2,2-dimethyl-11-isopropyl-1,11-diamino-undeca-4,8-diene (0.026 mol) and 21.0 g of oleic acid dimer ($C_{36}H_{68}O_4$; 0.037 mol) are pre-condensed in an autoclave for 120 minutes at 200°–250° C., then condensed further at 250° C. for 120 minutes, in a stream of nitrogen, and finally post-condensed for 1 hour in a high vacuum.

Polymer-Tg = −19° C., $\eta_{red}$ = 0.12 dl/g (0.5% solution in m-cresol at 25° C.).

EXAMPLE 10

15.82 g of 2,2-dimethyl-11-isopropyl-1,11-diamino-undecane-4,8-diene (purity: 99.5%; 0.0024 mol), 18.86 g of oleic acid dimer ($C_{36}H_{68}O_4$; 0.0334 mol), 4.28 g of adipic acid (0.0293 mol), 0.1 ml of a 10% aqueous $NH_4H_2PO_2$ solution and 0.2 g of di-tert.-butyl-p-cresol are condensed in an autoclave for 90 minutes at 250° C., in a nitrogen atmosphere.

Polymer-Tg = +14° C., $\eta_{red}$ = 0.24 dl/g (0.5% m-cresol solution at 25° C.).

EXAMPLE 11

Preparation of the polyamide from 1,2,3,6-tetrahydrophthaloyl chloride (THPC) and 2,2-dimethyl-11-isopropyl-1,11-diamino-undeca-4,8-diene (UDD)

A solution of 7.5 g of THPC in 100 g of $CH_2Cl_2$ is added dropwise, in the course of 1 hour, to a solution of 9.37 g of UDD (degree of purity: 97.5%) and 7.33 g of triethylamine in 315 g of $CH_2Cl_2$, which has been cooled to −15° C. The resulting solution is stirred for a further 90 minutes at −15° C. and 15 hours at +20° C. The solvent is stripped off, the residue is dissolved in 50 ml of ethanol and the polymer is precipitated in 4 liters of $H_2O$, filtered off, washed and dried in a high vacuum at 20° C.

Yield: 13.7 g (97.9% of theory), $\eta_{red}$ = 0.13 dl/g (0.345% solution in m-cresol at 25° C.).

Elementary analysis: C: 73.77% (theory: 74.57%), H: 9.94% (theory: 9.91%), N: 7.14% (theory: 7.25%).

Tg = 60° C.

Preparation of 1,2,3,6-tetrahydrophthaloyl chloride 17.4 g of 1,2,3,6-tetrahydrophthalic acid (0.1023 mol) and 42.5 g of phosphorus pentachloride (0.2040 mol) are placed in a bomb tube. The tube is tightly closed and shaken at 20° C. until the contents become fluid. After the excess pressure has been released, the tube is heated to 90° C. and the contents are allowed to react at this temperature for 3 hours. The product is isolated by distillation at $17.33.10^2$ Pa/133°–135° C. Yield: 13.0 g (61.4% of theory) Elementary analysis: C: 47.21% (theory: 46.41%), H: 4.11% (theory: 3.89%), Cl: 33.26% (theory: 34.24%).

EXAMPLES 12 TO 14

Polyamides from adipic acid and the diamine of the following formula

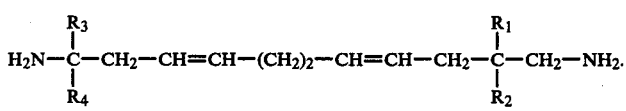

The substituents $R_1$–$R_4$ are as defined in Table II. The polyamides are prepared as described in Example 1. The reaction times and data relating to $\eta_{red.}$ and Tg of the polyamides are listed in Table II.

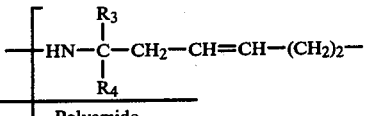
(I)

TABLE II

| Example | $R_1$ | $R_2$ | $R_3$ | $R_4$ | Purity of diamine (%) | Polyamide $\eta_{red}$ (dl/g) | Tg (°C.) |
|---|---|---|---|---|---|---|---|
| 12 | $CH_3$ | H | $CH_3$ | $CH_3$ | 96 | 0.32 | +35 |
| 13 | $CH_2$—$CH_3$ | $CH_2$—$CH_3$ | $CH(C_2H_5)_2$ | H | 95.4 | 0.31 | +54 |
| 14 | $CH_3$ | $CH_3$ | $CH_2$—$CH_3$ | H | 98.2 | 0.51 | +56 |

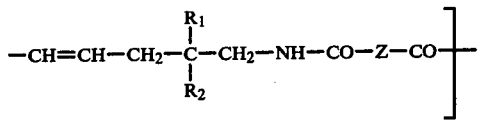

Application examples

I. A 10% solution in chloroform/ethanol (1:1) of the polyamide prepared according to Example I, which contains 5% by weight of cumene hydroxyperoxide, is coated with the aid of a 50 μm blade onto a copper printed circuit. The coating is dried for 3 minutes at 100° C., after which the layer thickness is about 5 μm. Subsequent hardening at 150° C. for 90 minutes in a nitrogen atmosphere gives a hard, transparent and shiny layer with good adhesion to the copper. If the circuit board treated in this way is left to stand for 72 hours in chloroform at 60° C., the polyamide is not dissolved and the adhesion of the polyamide is sufficient to prevent etching of the underlying copper. After storage for one week in water at 20° C., the coating retains its transparency and good adhesion to the copper; the water uptake is less than 1% by weight.

II.a 2.5 g of the polyamide obtained according to Example 1, 1.5 g of pentaerythritol tetrakis-(3-mercaptopropionate) and 95 mg of thioxanthone are dissolved in 10.8 ml of chloroform and the solution is applied with a 50 μm blade to a 100 μm thick polyester film. The coating is dried for 3 minutes at 100° C. and exposed with a 5,000 W high-pressure mercury lamp through a photographic mask for 15 seconds (distance of the high-pressure mercury lamp from the vacuum table: 70 cm). After developing for 30 seconds in chloroform, a well-resolved negative relief image is obtained.

b. The process described under (a) is repeated using 81.6 mg of benzophenone in place of the thioxanthone and using an exposure time of 60 seconds.

| Experiment | Exposure time (seconds) | Last step of which an image is formed on a 21 step sensitivity guide from the Stouffer Company |
|---|---|---|
| a | 15 | 8 |
| b | 60 | 8 |

What is claimed is:

1. A transparent polyamide which repeating structural units of the formula I in which $R_1$ is $C_{1-12}$-alkyl; $R_2$ is hydrogen or $C_{1-12}$-alkyl; $R_3$ is $C_{1-12}$-alkyl, cycloalkyl having 4–12 ring C atoms, aralkyl having 7 or 8 C atoms, substituted or unsubstituted aryl or, when $R_4$ is hydrogen, $R_3$ is also —CH=CH—alkyl or —C(alkyl)=CH—alkyl, each having 1–4 C atoms in the alkyl groups; $R_4$ is hydrogen, $C_{1-12}$-alkyl, cycloalkyl having 4–12 ring C atoms, aralkyl having 7 or 8 C atoms or substituted or unsubstituted aryl; or $R_1$ and $R_2$ or $R_3$ and $R_4$ together are alkylene having 3–11 C atoms; and Z represents at least one identical or different saturated or unsaturated aliphatic or aromatic divalent radical.

2. A polyamide according to claim 1 in which $R_1$ is $C_{1-5}$-alkyl, $R_2$ is hydrogen or $C_{1-5}$-alkyl, or $R_1$ and $R_2$ together are alkylene having 4–7 C atoms, $R_3$ is $C_{1-7}$-alkyl, $C_{5-8}$-cycloalkyl, unsubstituted phenyl or, when $R_4$ is H, $R_3$ is also —C($C_2H_5$)=CH—$CH_3$, $R_4$ is hydrogen or $C_{1-5}$-alkyl and Z is —m— or —p—phenylene, a saturated aliphatic divalent radical having 4 to 10 C atoms an unsaturated aliphatic divalent radical having 4–34 C atoms.

3. A polyamide according to claim 2 in which $R_3$ is $C_{1-5}$-alkyl, unsubstituted phenyl or, when $R_4$ is H, $R_3$ is also —C($C_2H_5$)=CH—$CH_3$, and $R_4$ is hydrogen or methyl.

4. A polyamide according to claim 1 in which $R_1$ is methyl or ethyl, $R_2$ is hydrogen, methyl or ethyl, $R_3$ is $C_{1-5}$-alkyl or unsubstituted phenyl, $R_4$ is hydrogen or methyl and Z is —m— or —p—phenylene or a saturated aliphatic divalent radical having 4–8 C atoms.

5. A polyamide according to claim 1 in which $R_1$ and $R_2$ are methyl, $R_3$ is isopropyl, $R_4$ is hydrogen and Z is —m— or —p—phenylene, or butylene.

6. A polyamide according to claim 1 in which $R_1$ and $R_2$ are methyl, $R_3$ is isopropyl, $R_4$ is hydrogen and Z is —p—phenylene in 50 to 90% of the structural units of the formula I and butylene in 50 to 10% of the structural units of the formula I.

7. The polyamide of claim 6 in which Z is —p—phenylene in 60 to 85% of the structural units of the formula I and butylene in 40 to 15% of the structural units of the formula I.

* * * * *